United States Patent
Liu et al.

(10) Patent No.: US 11,413,312 B2
(45) Date of Patent: Aug. 16, 2022

(54) METHOD OF TREATING DRY EYE SYNDROME WITH ADIPOSE-DERIVED MESENCHYMAL STEM CELLS

(71) Applicant: National Taiwan University, Taipei (TW)

(72) Inventors: I-Hsuan Liu, Taipei (TW); Chung-Tien Lin, Taipei (TW)

(73) Assignee: National Taiwan University, Taipei (TW)

( * ) Notice: Subject to any disclaimer, the term of this patent is extended or adjusted under 35 U.S.C. 154(b) by 392 days.

(21) Appl. No.: 16/702,559

(22) Filed: Dec. 4, 2019

(65) Prior Publication Data

US 2021/0169938 A1 Jun. 10, 2021

(51) Int. Cl.
| | | |
|---|---|---|
| A61K 35/28 | (2015.01) | |
| A61K 9/00 | (2006.01) | |
| A61K 47/02 | (2006.01) | |
| A61K 9/08 | (2006.01) | |
| A61P 27/04 | (2006.01) | |

(52) U.S. Cl.
CPC ............ *A61K 35/28* (2013.01); *A61K 9/0048* (2013.01); *A61K 9/08* (2013.01); *A61K 47/02* (2013.01); *A61P 27/04* (2018.01)

(58) Field of Classification Search
None
See application file for complete search history.

(56) References Cited

U.S. PATENT DOCUMENTS

| | | | | |
|---|---|---|---|---|
| 2014/0199275 A1* | 7/2014 | Murphy | ................... | A61P 27/04 604/272 |
| 2021/0046122 A1* | 2/2021 | Nishida | ................... | A61K 35/28 |
| 2021/0198631 A1* | 7/2021 | Lee | ...................... | C12N 5/0621 |

OTHER PUBLICATIONS

Beyazyildiz, E. et al. Efficacy of Topical Mesenchymal Stem Cell Therapy in the Treatment of Experimental Dry Eye Syndrome Model Stem Cells Int 1-9, 2014. (Year: 2014).*
Villatoro A. et al. Use of Adipose Derived Mesenchymal Stem Cells in Keratoconjunctivitis Sicca in a Canine Model. BioMed Res Int 1-10 2015. (Year: 2015).*
Al-Jaibaji O. et al. Mesenchymal Stromal Cells for Ocular Surface Repair. Expert Opinion on Biolgical Therapy 19(7)643-653, Apr. 2019. (Year: 2019).*
Dietrich, J. et al. MSC Transplantation Improves Lacrimal Gland Regeneration After Surgically Induced Dry Eye Disease in Mice. Scientific Reports 9(1)18299 2019. (Year: 2019).*
Bittencourt, M. et al. Veterinary Clinical Investigations: Use of Heterologous Mesenchymal Stem Cells in Dogs with Keratoconjunctivitis Sicca. Investigative Ophthalmology and Visual Science 55(13)3677 Apr. 2014. (Year: 2014).*
Lee, M. et al. Mesenchymal Stem/Stromal Cells Protect the Ocular Surface by Suppressing Inflammation in an Experimental Dry Eye 23(1)139-146 Jan. 2015. (Year: 2015).*
Aluri H. et al. Delivery of Bone Marrow Derived Mesenchymal Stem Cells Improves Tear Production in a Mouse Model of Sjogrens Syndrome. Stem Cells Int 1010, 2017. (Year: 2017).*
Zhang, C., et al., Research Progress of Mesenchymal stem cells in the treatment of dry eye, New Advances in Ophthalmology, 2017-3-289-292 Publication, Date Mar. 5, 2017, ISBN: 1003-5141, CN: 41-1105/R.

* cited by examiner

*Primary Examiner* — Ralph J Gitomer
(74) *Attorney, Agent, or Firm* — Hannah Tien

(57) ABSTRACT

The present invention provides a method of treating a subject suffering from dry eye syndrome, comprising: administering to said subject a pharmaceutical composition for treating dry eye syndrome, comprising an effective amount of adipose-derived mesenchymal stem cells and the pharmaceutical composition is administered to the eye topically in the form of eye drops.

8 Claims, 14 Drawing Sheets

A

B

C

D

METHOD OF TREATING DRY EYE SYNDROME WITH ADIPOSE-DERIVED MESENCHYMAL STEM CELLS

FIELD OF THE INVENTION

The present invention relates to a method of adipose-derived mesenchymal stein cells for treating dry eye syndrome.

BACKGROUND OF THE INVENTION

Keratoconjunctivitis sicca (KCS) or dry eye syndrome (DES) is one of the recognized eye diseases of human as well as canine patients. The main key to dry eye syndrome is excessive evaporation of tear fluid and insufficient secretion of tear fluid. KCS is characterized by the development of ocular surface damage. There are many causes, which can be basically divided into the following two categories: the first category is caused by insufficient secretion of tear fluid, including "insufficient secretion of primary tear fluid" and "insufficient secretion of secondary tear fluid." The cause of "insufficient secretion of primary tear fluid" is unknown, and "insufficient secretion of secondary tear fluid" is common in "dry syndrome" caused by rheumatoid immune diseases such as "rheumatoid arthritis," for example, Sjogren's syndrome (SS) is highly correlated with KCS, the typical symptoms of SS is a combined symptom of dry eyes and dry mouth. Dry eyes can cause light sensitivity, chronic irritation, destruction of corneal epithelium, and eye sensitivity, as a result, the quality of a patient's life is significantly affected. In addition, KCS can be a primary or a secondary phenomenon and coexists with various types of systemic autoimmune diseases, for example, any conditions that reduces corneal sensitivity, such as diabetes, computer use, contact lens wear, menopause, air conditioning and smoking, can increase the risk of dry eyes. The second category is caused by excessive evaporation of tear fluid. Patients with this category of dry eye syndrome include long-term eyelid inflammation, normal but large surface area of eye cracks, thyroid eye disease.

KCS is defined as an inflammatory disease of cornea and conjunctiva. The development of ocular surface damage is a secondary factor of pre-corneal tear film deficiency. The tear film has five important functions, including: protecting the eyes from external stimuli, lubricating the eyes to relieve discomfort, washing away foreign objects on the eyes and keeping the eyes smooth, reducing the risk of eye infections and providing oxygen and nutrients. In canine patients, KCS is defined as inflammation of cornea and conjunctiva, secondary to pre-corneal tear film deficiency. Tear film defects or deficiency may result in the following conditions, including recurrent corneal ulcers or ocular trauma, dehydration of the corneal and conjunctival epithelium, chronic surface irritation, secondary infection, and malnourished corneal and conjunctival epithelium. At an early stage, significant serous secretions may appear in the eyes. As the disease progresses, the secretion becomes a viscous mucus with a yellow to green appearance. In addition, chronic inflammation of the ocular surface not only causes redness, pain and inflammation of the eyes, but also causes corneal scar formation, new blood vessel formation, hyperpigmentation and hyperkeratosis of the corneal epithelium. In the final stage of KCS, these corneal changes may lead to impaired vision or even vision loss. Due to tear film deficiency, KCS can be divided into quantitative KCS and qualitative KCS, in which quantitative KCS is a decrease or lack of water content in the tear film, which is more common in veterinary patients. The etiology of KCS in canine animals includes congenital, metabolic, infectious, drug-induced, neurogenic, radiological, iatrogenic, and the most common cause is idiopathic KCS (iKCS). iKCS is generally considered to be immunological, and may be autoimmune disease pathogenesis. Therefore, more and more studies use immune-mediated KCS to replace iKCS.

For clinical diagnosis, in human patients, the recommended sequence of KCS diagnostic tests is: medical history and examination, followed by a symptom questionnaire, the tear film break-up time, an ocular surface fluorescein stain test, a Schirmir test, eyelid and tarsus morphology and tarsus expression. In canine patients, the diagnosis of KCS is divided into tear production test, tear quality and clinical signs. The classic test for tear production is the Schirmer tear test (STT), which includes measurement of the amount of tear absorption by a strip of filter paper within one minute to assess the production of aqueous tear fluid. Recent studies have shown that dogs with a STT test result of 15-20 mm/min is considered normal, while dogs with 10 to 15 mm/min may be considered as subclinical dry eye syndrome. The quality of tear fluid can be measured indirectly by using fluorescein and the tear film break-up time (TBUT). TBUT is mainly used to evaluate conditions concerning tear fluid evaporation and nasal tear drainage. The test method is to inject fluorescein into the tear film of a patient, and then manually open the eyelid to observe the tear film under wide cobalt blue illumination while the eye is not blinking. The TBUT record is the time (seconds) required for the first dry spot to appear in the tear film. A TBUT of less than 15 seconds is considered abnormal. An increase in tear osmolarity is common to all types of KCS because excessive evaporation of the fluid naturally increases the osmolarity and ion concentration of the tear film. Excessively high ion concentration in the tear film is considered to be important in the pathogenesis of various dry eye diseases. i-PEN® is a novel technical device, wherein a disposable osmolarity test sensor is inserted into the i-Pen® system, the tip of the sensor is pressed against the conjunctiva of the lower eyelid, and then the osmolarity of the tear fluid is analyzed through its conductivity. When the i-Pen® Vet osmolarity test sensor is used, the osmolarity of tear fluid of a normal canine patient ranges from 296 to 339 mOsms/L. In addition, a slit-lamp biomicroscopy and a fluorescein stain test are used to evaluate clinical signs. The fluorescein stain test is mainly used to detect corneal ulcers, corneal erosion and other ocular surface changes. In short, quantitative KCS is mainly determined on the basis of clinical signs, the fluorescein stain and the STT test result which is no more than 10 mm/min.

Dry eye syndrome can be treated with eye-lubricating eye drops or ointments, and severe dry eye syndrome can be treated with 0.05% cyclosporin. Most patients require systemic treatment, including pilocarpine, non-steroidal anti-inflammatory drugs (NSAIDS), and immunosuppressants, such as Methotrexate (MTX), Hydroxychloroquine, Rituximab, and Glucocorticoids. With respect to medical treatment of KCS, topical antibiotics, topical anti-inflammatory drugs and mucolytic agents are used in some cases, but most canine KCS patients require long term topical treatment. It is veterinarians' obligation to educate dog owners about KCS chronic diseases and the necessity of life-long eye drops. Tear substitutes are used in eye drops for lubricating dry eyes, which can be used as a solution, a gel and an ointment. In order to achieve a more intense and long lasting effect, most canine KCS patients cannot use artificial tears as monotherapy because it requires frequent uses to achieve the desired lubricating effect. Artificial tears usually contain water, salt supplements and polymers, which are mainly used to maintain ion balance of the tear film and function as a lubricant to reduce discomfort, while increasing the viscosity, the retention time of artificial tears on the ocular surface and the mucoadhesive force. Some artificial tear formulas contain vaseline, mineral oil, castor oil, glycerin or lanolin, which can provide long-term lubricating effect, but also leads to debris buildup. These artificial tears can be used in patients with insufficient lipid layer or suffering from blepharitis, however, preservatives such as ammonium benzyl chloride should be avoided because they tend to cause toxic epithelial damages and exacerbate inflammation.

In addition, immunosuppressants are used in patients with advanced KCS, these immunosuppressants have the effect of anti-inflammation, pigmentation reduction, normalization of goblet cell mucin secretion and direct stimulation of tear secretion. Topical immunosuppressants are eye drops used to restore tear production. Topical use of cyclosporine increases the production of tear fluid, significantly reduces chronic corneal neovascularization, mucinous conjunctivitis, and enhances rapid healing of refractory corneal ulcers. It is believed that cyclosporine has the immunomodulatory ability to inhibit the proliferation of T helper cells and cytotoxic T cells in the lacrimal gland by blocking the production of interleukin 2 and to allow normal tear fluids. Cyclosporine is a highly lipophilic drug and therefore needs to be topically used in a lipid vehicle, olive oil or corn oil was used as a diluent at the beginning Cyclosporine is commercially available as a 0.2% ointment (Optimmune, Merck Animal Health, USA). The concentration of cyclosporine for human patients is recommended to be between 0.05% and 1%, and between 0.2% and 2% for canine patients. As for the effect of cyclosporine treatment, approximately 80% of the dogs with STT≥2 mm/min had an increase in tear secretion, and approximately 50% of the dogs with STT<2 mm/min reacted to the treatment. An aqueous suspension of 0.02% tacrolimus was used in one study to study its effect on tear production in canine KCS patients, the results showed that 0.02% tacrolimus aqueous suspension administered orally twice daily had the effect of tear stimulation and could be a substitute for topical cyclosporine. Another study showed that in cases of advanced canine KCS, the therapeutic effect of tacrolimus might be better than cyclosporine and no oversensitive reactions were observed. Therefore, tacrolimus is suitable for patients with low tolerance to cyclosporine. Although a variety of immunosuppressants have been used in the treatment of KCS, many canine KCS patients do not respond to immunosuppressive therapy. Therefore, there is a need to develop alternative drugs or treatment method for the treatment of KCS.

DETAILED DESCRIPTION OF THE INVENTION

Canine dry eye syndrome is caused by autoimmunity, and dogs suffering from dry eye syndrome have always been regarded as an important animal model of autoimmune diseases. In the past, canine dry eye syndrome was controlled by immunosuppressive eye drops, but the therapeutic effect was limited. There have been several studies in the past three years, showing that the treatment of periocular injections of stein cells has positive effects, therefore the immunomodulatory effect of mesenchymal stein cells is expected to bring new opportunities for this disease. However, clinically, periocular injection requires sedation or even general anesthesia, and it may also cause iatrogenic injury during the injection process. Therefore, the present invention provides an effective treatment of canine patients suffering from clinical dry eye syndrome by using a non-invasive, topical eye-drop administration method.

In the present invention, adipose-derived mesenchymal stein cells (Ad-MSC) were successfully isolated first, and then the properties of trilineage differentiation and immunomodulation were confirmed, and proper preservation methods of the prepared eye drops were tested. In the clinical trial of the treatment, patients were divided into two groups based on their prior uses of immunosuppressant eyedrops, and stein cell eye drops were given once a week for six consecutive weeks, and ophthalmic examinations were performed before treatment (baseline), during treatment (week 3 and week 6), and after treatment (week 9), including a tear fluid secretion test, a corneal fluorescein stain test, and tear film break-up time, and a tear fluid osmolarity test, and clinical changes were assessed through secretions, conjunctival hyperemia, and the severity of corneal lesions. The amount and quality of tear fluid were significantly improved after treatment with stein cells eye drops. More than half of the treated patients had an increased amount of tear fluid, even in the group of those patients who did not respond to immunosuppressants in the past, 56.5% of them had an increased amount of tear fluid, and when clinical symptoms were reduced and slowed down, these animals were more comfortable with their eyes and the quality of their lives were improved. Based on the above results, continuous treatment of adipose-derived mesenchymal stein cells for six consecutive weeks has the potential to become an alternative to the traditional treatment of canine dry eye syndrome. As compared to traditional treatment, which requires two to three times a day of long-term and frequent administrations, the stein cells treatment only requires a course of six times of administration. For owners who are unwilling to cooperate or for dog patients who have poor response to immunosuppressants, topical administration of adipose-derived mesenchymal stein cells can improve dry eye syndrome of the dogs, and the therapeutic effect of one course of treatment can last for one year of longer.

Accordingly, the present invention provides a use of a pharmaceutical composition for preparing a medicament for treating a subject suffering from dry eye syndrome, wherein the pharmaceutical composition comprises an effective amount of adipose-derived mesenchymal stein cells, and the drug is in the form of an eye drop. According to one aspect of the present invention, it provides a use of a pharmaceutical composition for preparing a drug for treating a subject suffering from dry eye syndrome, wherein the pharmaceutical composition comprises an effective amount of adipose-derived mesenchymal stein cells or pharmaceutically acceptable salts or carriers thereof.

According to one aspect of the present invention, it provides a method of treating a subject suffering from dry eye syndrome, comprising: administering to said subject a pharmaceutical composition for treating dry eye syndrome, comprising an effective amount of adipose-derived mesenchymal stein cells, wherein the pharmaceutical composition is administered to the eye topically in the form of eye drops.

In one embodiment, the dry eye syndrome is an immune-mediated dry eye syndrome. In another embodiment, wherein the immune-mediated dry eye syndrome is Sjogren's syndrome. In one embodiment, wherein the subject is a mammal; in another embodiment, wherein the mammal is selected from the group consisting of a human, a dog, a cat, a horse, a rabbit, a mouse, a pig, a cow, a sheep, a monkey, a baboon, and a gorilla; in another embodiment, wherein the mammal is a human; in another embodiment, wherein the mammal is a dog.

In the pharmaceutical composition of the present invention, in one embodiment, wherein the source of the adipose-derived mesenchymal stein cells is a subject that is allogeneic to the subject. In another embodiment, the subject from which the adipose-derived stein cell is derived is a dog, and the subject suffering from dry eye syndrome is another dog.

In the pharmaceutical composition of the present invention, in one embodiment, wherein the solution of the eye drop is phosphate buffered saline. In one embodiment, wherein the concentration of the effective amount of adipose-derived mesenchymal stein cells is from $1 \times 10^6$ to $5 \times 10^6 / 50$ μL. In another embodiment, wherein the concentration of the effective amount of adipose-derived mesenchymal stein cells is $2 \times 10^6 / 50$ μL. In one embodiment, wherein the eye drop is administered once a week for at least three consecutive weeks or longer. In another embodiment, wherein the eye drop is administered once a week for at least six consecutive weeks or longer.

In one embodiment, wherein the subject suffering from keratoconjunctivities sicca is a subject who does not respond to an immunosuppressive therapy. In one embodiment, wherein the immunosuppressive therapy comprises a treatment with cyclosporine A, pimecrolimus or tacrolimus or any combination thereof.

EXAMPLES

Figure 1:
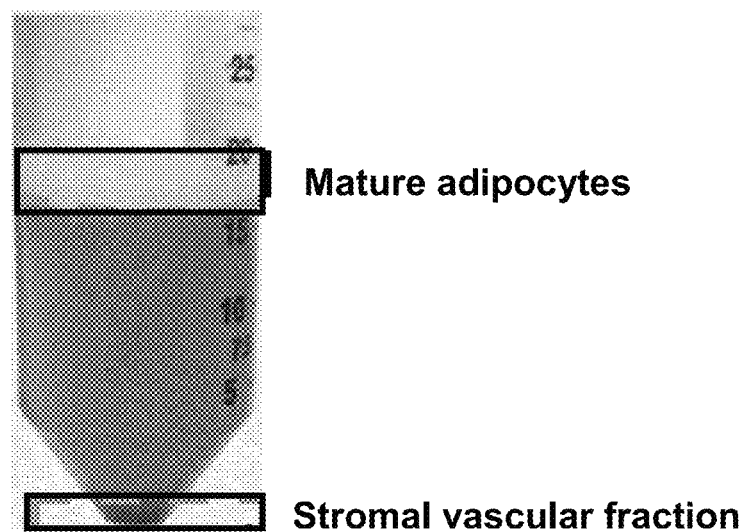
FIG. 1. Isolation and purification of stromal vascular fractions. Mature adipocytes in the supernatant were separated by centrifugation of the sample and precipitated into stromal vascular fraction (SVF), wherein SVF contains a heterogeneous cell population, including mesenchymal stein cells, adipose precursor cells, vascular endothelial cells, and fibroblasts, etc.

The following examples are merely illustrative of the invention, but the scope of protection of the invention is not limited to the following examples. In order to make the above and other objects, features and advantages of the present invention comprehensible, the following examples are provided with detailed description as follows:

Example 1. Preparation of Adipose-Derived Mesenchymal Stem Cells

Material and Method
1. Inclusion Criteria for Donors:

The National Taiwan University Institutional Animal Care and Use Committee (IACUC number: NTU106-EL-00097) and the National Taiwan University Veterinary Hospital (Clinical Research No.: 000031) approved the experimental plan for adipose tissue separation. The donors included in this study were canine patients at the National Taiwan University Veterinary Hospital (NTUVH), the owners of these patients consented to participate in the donation of adipose tissues. The inclusion criteria for canine blood donors among canine donors were modified, requiring donors to meet the following specific criteria: (1) between 1 and 8 years of age; (2) body weight exceeding 5 kg and body condition score (BCS) ⅗ or above; (3) the latest vaccination being received; (4) no history of blood-borne diseases; (5) healthy, no medication. All abdominal operations were performed under general anesthesia.

2. Separation of cAD-MSC:

Adipose tissues were collected from omental adipose tissues of the dogs using the standard sterile surgical procedure. Samples were collected in sterile 50 mL tubes and 10 mL of Dulbecco's Modified Eagle Medium (DMEM) medium containing 3.7 mg/mL of sodium bicarbonate, 100 U/mL of penicillin, and 100 g/mL of streptomycin was added. The samples could be stored at room temperature for up to 24 hours prior to use. In this study, the separation procedure was performed immediately after the samples were collected. The adipose tissue samples were weighted and then trimmed with a cutting shear in a biosafety cabinet. An equal volume of pure medium was added for repetitive aspirations to wash the tissues, and 1 mg/mL of collagenase type IA was added, then placed in an incubator at 37.5° C., 95% of humidity and 5% of $CO_2$ for 1 hour of reaction. After the reaction had completed, the collagenase activity was neutralized by adding an equal volume of 10% heat-inactivated fetal bovine serum medium. The neutralized sample was centrifuged at 2000 RPM for 5 minutes. After separation, the supernatant contained mature adipocytes, and the precipitated fraction was the stromal vascular fraction (SVF). The precipitated fraction (i.e., SVF) was removed and reacted with erythrocyte lysis buffer solution (0.15 M of $NH_4Cl$, 1 mM of $KHCO_3$, 0.1 mM of $Na_2EDTA$, pH 7.3) for 10 minutes to lyse the erythrocytes. The completely reacted sample was thoroughly washed by adding the medium, filtered through a 70 μm nylon cell strainer, and the centrifugation step was repeated. The cell pellets were resuspended in the medium and the number of cells in each ml of the cell suspension was estimated, the cells at a density of $1 \times 10^4$ cells/cm' were inoculated in a 100 mm culture dish, and incubated in a 5% CO2 incubator at 37.5° C., the medium was changed once every three days.

3. Passaging, Cryopreservation and Reviving Procedure of cAD-MSC:

Since mesenchymal stein cells had plastic adhesion characteristics under normal culture conditions, the non-adherent cells could be removed by changing the medium once every three days. The medium was refreshed once every three days until the cell density was approximately 70-80%. The medium was removed and the culture dish was rinsed with a pre-warmed phosphate buffer solution, and allowed for reaction with 0.25% trypsin-EDTA at 37.5° C. for at least 2 minutes. The adherent cells were detached, and after most of the cells were separated from the bottom of the culture dish, the activity of the enzyme was neutralized by adding an equal volume of serum-containing medium. The neutralized cell suspension was centrifuged at 1200 RPM for 5 minutes to precipitate the cells. For subculture, the precipitated cells were cultured at a ratio of 1:2 to 1:3. When cryopreservation was to be carried out, the supernatant was carefully removed, and the precipitates were resuspended in a cryopreservation medium consisting of 90% of FBS and 10% of dimethyl sulfoxide and diluted into a cryopreservation medium having a final concentration of $5 \times 10^4$ cells/mL The cells were transferred to polypropylene cryotubes and labeled, placed in a freezer, frozen in a refrigerator at −80° C. for three days, and then transferred to a liquid nitrogen container for long-term storage. As for the reviving of cAD-MSC, the cryotubes were withdrawn from the liquid nitrogen and immediately placed in a water bath of 37° C. The cryopreserved cells were then rapidly thawed for 1-2 minutes. To avoid cytotoxicity generated in DMSO, the tubes should be removed from the water bath when about 80% was thawed. The thawed cells were mixed with 9 mL of growth medium through gentle suction. After centrifugation at 1200 RPM for 5 minutes, the cryoprotective solution was removed and the cells were gently resuspended in 2 mL of medium and inoculated in a 35 mm culture dish.

4. Determination of Colony Forming Unit (CFU) of cAD-MSC:

To analyze the colony formation efficiency of cAD-MSCs, the cells were cultured in the culture medium of a 6-well culture plate at two different seeding densities (350 and 500 cells/cm') for 10 days. The cells were washed with PBS and fixed with methanol for 5 minutes, then stained with Giemsa for 20-30 minutes, rinsed with deionized water, and colonies having a diameter of 2 mm or more were counted as the colony forming unit.

5. Trilineage Differentiation of cAD-MSC:

To observe the pluripotent differentiation potential of mesenchymal stein cells, the ability of cAD-MSC cells to differentiate into adipocyte cell lines, chondrocyte cell lines, and osteoblast cell lines was analyzed. For osteoblast differentiation, cells were seeded in a 35 mm culture dish at a seeding density of 1000 cells/cm² and treated with osteogenic induction medium for about 7-10 days, and the osteogenic induction medium was changed once every 3 days, and the medium was composed of a medium (DMEM and 10% FBS) supplemented with 50 μM of L-ascorbic acid 2-phosphate, 10 mM of β-Glycerophosphate and 0.1 μM of dexamethasone. Osteogenesis was evidenced by extracellular mineralized calcium phosphate deposits, and the cells were stained with 40 mM of Alizarin Red S for 15 minutes, washed with PBS and fixed with 10% formaldehyde and then the evaluation was conducted. For chondrogenic differentiation, $2.5 \times 10^5$ cells were seeded in a 15 mL centrifuge tube, and after being centrifuged at 300 g for 5 minutes, the cells were cultured in a chondorcyte induction medium for about 30 days, and the chondrocyte induction medium was changed once every 3 days. The chondrocyte induction medium was composed of a pure medium (DMEM) supplemented with 1% FBS, 10 ng/mL of transforming growth factor β1 (TGF-β1), 6.25 μg/mL of insulin, and 50 nM of L-ascorbic acid 2-phosphate. The next day the cells became spherical and the cells aggregated more in the following day. Upon completion of the cultivation, the spherical micelles were fixed in 10% formaldehyde for 1 hour and then placed in a suitable marker box for paraffin sections. The thickness of the paraffin sections was 5 μm or 6 μm. The slides were immersed in xylene twice for 15 minutes and then washed in 100%, 90%, 80%, 70% and 60% ethanol for 5 minutes, the slides were rinsed with PBS for 5 minutes, and the above steps were repeated one more time. The 6 μm slides were stained with 0.1% toluidine blue O for 5 minutes, while 5 μm slides were stained with 1% Alcian blue. After staining, the samples were washed with PBS and protected and preserved with a fixing medium. The accumulation of sulfated glycosaminoglycans (GAG) was determined after the staining was evaluated under a microscope. For adipogenic differentiation, the cells were seeded in a 35 mm culture dish at a density of 10,000 cells/cm' for cultivation. The cells were full and reached saturation after 3-5 days of culture, the medium was replaced with an adipogenic medium, cultured for 35-40 days, and the adipogenic medium was changed once every three days. The adipogenic medium was composed of a medium (DMEM and 10% FBS) supplemented with 1 μM of dexamethasone, 10 μg/mL of insulin, 100 μM of indomethacin, and 0.5 μM of isobutylmethylxanthine (IBMX). The culture dish was fixed in 10% formaldehyde for 10 minutes and replaced with 1 mL of propylene glycol for 1 minute to absorb excessive water. The cells were immersed in 200 μL of 0.5% Oil Red O for 15 minutes to stain the lipid droplets, and then replaced with 1 mL of 60% propylene glycol aqueous solution. The culture dishes were carefully washed once with deionized water and evaluated under a microscope.

6. Immunophenotype of cAD-MSC:

A Coulter Cytomics FC500 flow cytometer was used to analyze the surface marker expression of canine adipose-derived mesenchymal stein cells. To prepare antibody staining, 1 μL of the fluorescently coupled antibodies was mixed with 49 μL of a wash buffer solution consisting of PBS and 1% FBS, and the diluted and mixed antibodies were placed on ice in the dark. The cells were washed twice with PBS and separated with 0.25% trypsin-EDTA at 37.5° C. for at least 2 minutes, and the enzyme activity was neutralized by adding an equal volume of medium. The cells were transferred to 15 mL centrifuge tubes and the tubes were centrifuged at 1200 RPM for 5 minutes to precipitate the cells. The precipitated cells were resuspended in a wash buffer solution and filtered through a 70 μm nylon cell strainer. $2\times10^5$ cells in 50 μL of wash buffer solution were mixed with 50 μL of the diluted and mixed antibodies, and allowed for reaction in the dark at 4° C. for at least 30 minutes. The residual antibodies were removed by being washed with a wash buffer solution and centrifuged at 2000 RPM for 5 minutes. After being centrifuged, the cells were resuspended in a fixation buffer solution at a concentration of $10^5$ to $10^6$ cells/mL, the buffer solution was composed of PBS, 1% FBS and 3% formaldehyde, and then subjected to flow cytometry analysis.

7. Immunomodulatory Effect of cAD-MSC:

To observe the immunomodulatory properties of canine adipose-derived mesenchymal stein cells, the ability of the mesenchymal stein cells to inhibit proliferation of mononuclear cells under mitogenic stimulation was analyzed. First, cAD-MSC cells were treated with 10 μg/mL of mitomycin C for 2 hours in the dark at 37° C., then the cells were detached by being treated with 0.25% trypsin-EDTA, and the enzyme activity was neutralized by a medium, the cell concentration was then counted. The cells were seeded into a 96-well plate at a concentration of $1\times10^5$, $5\times10^4$, $2.5\times10^4$, $1.25\times10^4$, $6.25\times10^3$, $3.125\times10^3$, $1.56\times10^3$, $7.8\times10^2$, and 390 cells in 50 μL and cultured for at least 6 hours. Canine whole blood was collected from dog donors of the NTUVH through intravenous route and stored in tubes containing ethylenediaminetetraacetic acid (EDTA). The blood sample was centrifuged at 1200 RPM for 10 minutes, then the supernatant was carefully removed and the precipitated cells were resuspended in an equal volume of pre-warmed RPMI-1640 medium, the medium contained 20% FBS, 100 U/mL of penicillin, 100 μg/mL of streptomycin, 50 μM of 2-mercaptoethanol, and 55 μM of Ficoll-Paque, and mononuclear cells were obtained by cell density gradient centrifugation. In short, 6 ml of Ficoll-Paque medium was added into a 15 mL centrifuge tube, then the diluted blood sample was carefully spread on the Ficoll-Paque medium solution, and the centrifugation was started at 500 RPM, which was increased by an increment of 100 RPM for every 30 seconds, up to 1700 RPM after 20 minutes. After centrifugation, different layers were separated according to the density, including plasma, buffer layer, Ficoll-Paque medium, and red blood cells. The buffer layer containing peripheral blood mononuclear cells (PBMC) was transferred to a sterile centrifuge tube and washed with at least 3 mL of RPMI-1640 medium. Finally, these mitomycin C-treated cAD-MSCs were co-cultured with $1\times10^5$ canine PBMC cells and 5 μg/mL of concanavalin-A (ConA) was used in each well of a 96-well plate for mitotic stimulation. Canine PBMCs stimulated by mitotic ConA were used as the positive control. After four days of culture, the total number of cells was analyzed by a Cell Counting Kit 8 (CCK-8). 10 μL of CCK-8 solution was added to each well and allowed for reaction in an incubator for 2 hours according to the instructions provided in the instruction manual in the kit. The absorbance at 450 nm was read with an ELISA reader, and the cell proliferation index was calculated relative to the absorbance reading (OD) of the group of positive control.

8. Preparation of cAD-MSCs Eye Drops and Confirmation of their Survival Rate:

The cells were separated by trypsin-EDTA solution and the enzyme activity was neutralized with an equal volume of medium. The suspension was transferred to a 15 mL centrifuge tube and then centrifuged at 1200 RPM for 5 minutes to precipitate the cells, and the supernatant was carefully removed. The precipitated cAD-MSCs were formulated with phosphate buffered saline (PBS) into a suspension solution of $2\times10^6$ cells/50 μL, and aseptically filled into a sterile 1 mL disposable syringe. 2 hours prior to topical administration, the activity of the passage 4-6 of cAD-MSCs were resuscitated by the above-described method. The trypan blue exclusion test was used to assess the survival rate of cAD-MSCs in PBS. The formulated 10 μL of eye drops containing cAD-MSCs was gently mixed with an equal volume of 0.4% trypan blue, and then added to a hemocytometer to count viable cells (unstained) and non-viable cells (stained). The eye drops containing cAD-MSCs were stored in the dark at 4° C. and room temperature, and the percentage of viable cells was counted once every hour to calculate the survival rate.

Results

Figure 2:
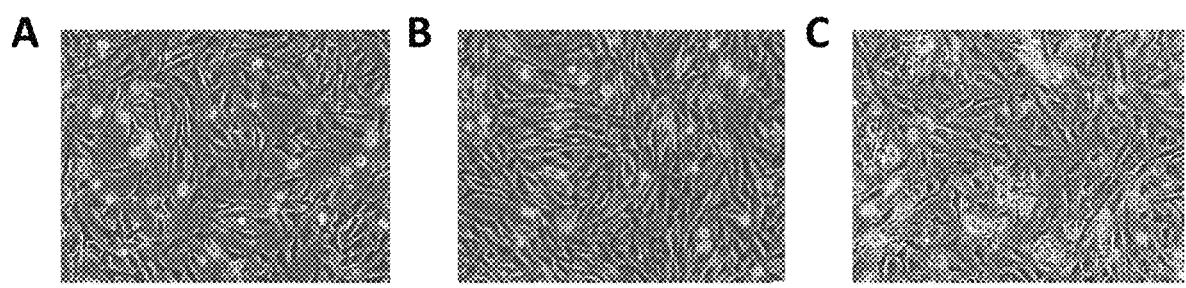
FIG. 2. Phenotype of adipose-derived mesenchymal stein cells. (A) The fibroblast-like cells with abilities to adhere to culture dish and growth are observed in primary culture; (B) on the second day of culturing, the same pattern remained and the cell density reaches saturation; (C) cell phenotypes of the second passage of cAD-MSCs.

1. Preparation of Canine Adipose-Derived Mesenchymal Stem Cells:

During the study from October 2017 to April 2018, five clinically healthy female dog donors who were of different breeds, from 1.5 to 6 years of age, from 2 to 23 kg of body weight, and had undergone ovarian hysterectomy were included. Omental adipose tissues were successfully obtained from each donor (FIG. 1). The ability of having fibroblast-like cells and the ability of adhering the culture dish to grow were observed in the primary culture (FIG. 2A). The same pattern was maintained in the second day, and the growth density reached saturation 2-3 days after the passage (FIG. 2B) and had the ability to passage and to maintain its cell morphology (FIG. 2C).

Figure 3:
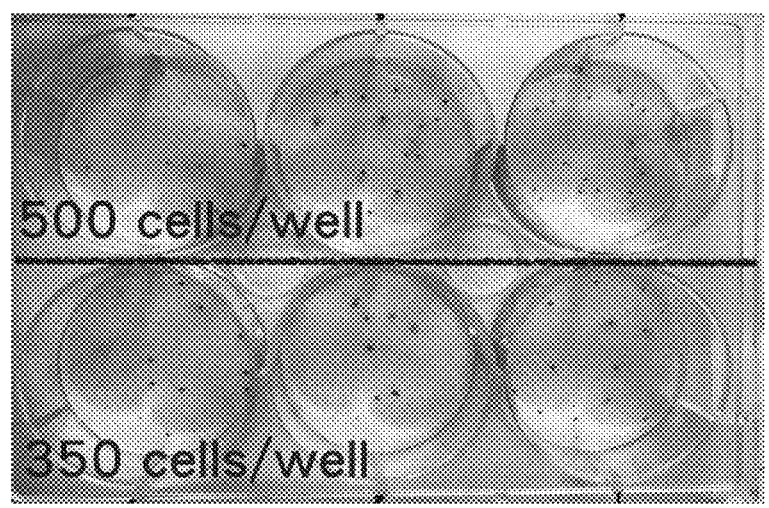
FIG. 3. Determination of the number of colony forming units of cAD-MSCs. When the seeding density is 500 cells/cm², the number of colony forming units is 15.3±2.3, and the number of colony forming units is 12.0±3.6 when the seeding density is 300 cells/cm'.

2. Determination of Colony Forming Units:

The cells isolated from omental fat formed colonies on the plastic surface in the DMEM containing 10% FBS. When the seeding density was 500 cells/cm$^2$, the number of colony forming units was 15.3±2.3 (n=6), and when the seeding density was 300 cells/cm$^2$, the number of colony forming units was 12.0±3.6 (n=6) (FIG. 3).

Figure 4:
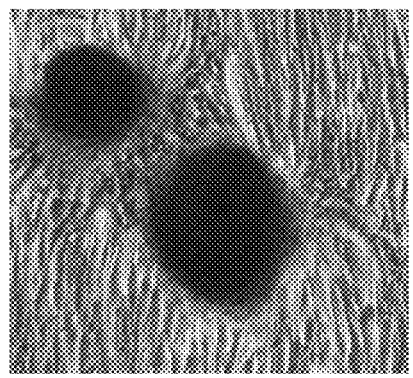
FIG. 4. Trilineage differentiation of cAD-MSCs. (A) Osteogenic differentiation of cAD-MSCs, in which alizarin red S staining shows an extracellular mineralized matrix, so called bone nodules; (B-C) chondrogenic differentiation of cAD-MSCs, the micelles are cut into thin slices and stained with 0.1% Toluidine blue O (B) and 1% Alcian blue stain (C), the results show typical glycosaminoglycan accumulation; (D) adipogenic differentiation of cAD-MSC, lipid droplets are stained with oil red O as positive.
Figure 4:
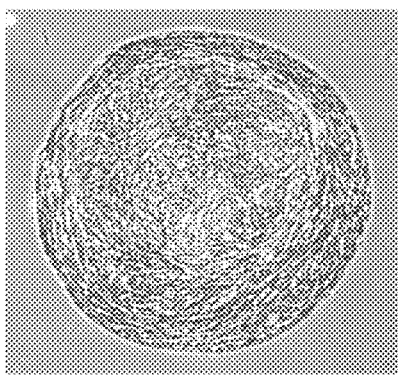
Figure 4:
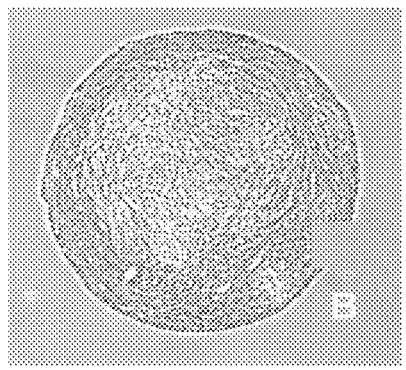
Figure 4:
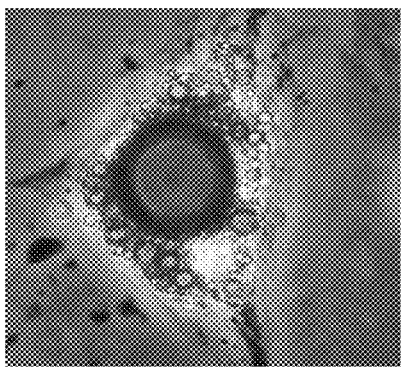

3. Trilineage Differentiation Capacity of Adipose-Derived Mesenchymal Stem Cells:

The plasticity of CADI-MSCs was evaluated by trilineage induction, including osteogenic, chondrogenic and adipogenic differentiation, which were evaluated by accumulation of extracellular calcium phosphate, sulfated glycosaminoglycans, and lipid vacuoles, respectively. Osteogenic differentiation: After 3-4 days of culture with osteogenic induction medium, the formed cell pattern of white nodule-like colonies was observed, which lasted for 7 days under osteogenic conditions. These white nodule-like colonies were strongly stained with alizarin red S staining (FIG. 4A), so-called extracellular mineralized matrix of bone nodules. Chondrogenic differentiation: In the chondrogenic induction medium, the cells were spherical on day 2 and smaller and more aggregated micelles were formed after 10 to 15 days of culture, and after 30 days of culture, the micelles were sliced into thin slices and stained with 0.1% toluidine blue O and 1% Alcian blue, the results showed typical glycosaminoglycan accumulation (FIGS. 4B and 4C). Adipogenic differentiation: The cells were cultured at a density of 10,000 cells/cm', when the density of the cultured cells reached saturation, they were transferred to an adipogenic induction medium, at this time the cells stopped growing, and after 15-20 days of culture the cells began to be filled with small vacuoles, until they were cultured for 30 days these small vacuoles appeared to have been engulfed as droplets stained with 0.5% oil red O. The results showed that the droplets stained with oil red O was positive (FIG. 4D).

Figure 5:
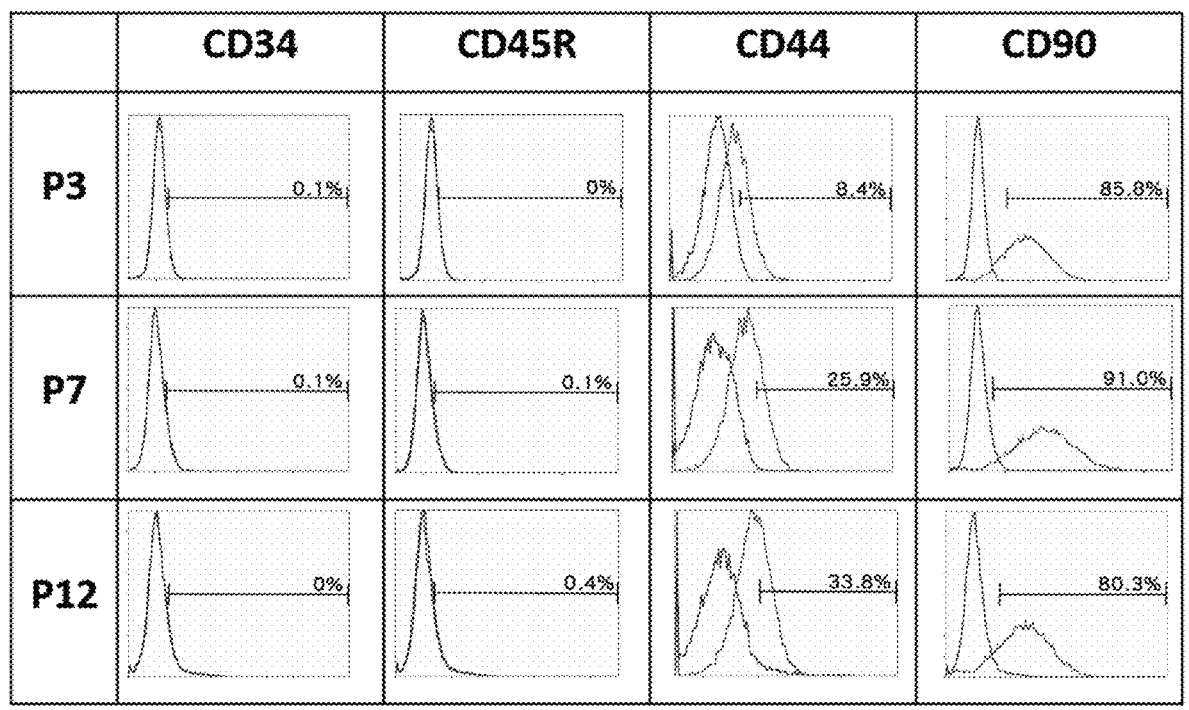
FIG. 5. Detection of the expression of surface molecules of cAD-MSCs. In the passage 3, 7 and 12 of cAD-MSCs, the expression of CD34 and CD45 are negative, but most of the cAD-MSCs express CD90 (Thy1) adherent molecules and also moderately expresses CD44. In additon, the percentage of CD44 expressing cAD-MSCs increases as the number of passage increases.

4. Immunophenotype of Adipose-Derived Mesenchymal Stem Cells:

The passage 3, 7, and 12 of cAD-MSCs were negative CD34 and CD45 expression, but most of cAD-MSCs were positive CD90 (Thyl) expression and moderately CD44 expression. The percentage of CD44 expressing cAD-MSCs increased as the number of subcultures increased (FIG. 5).

Figure 6:
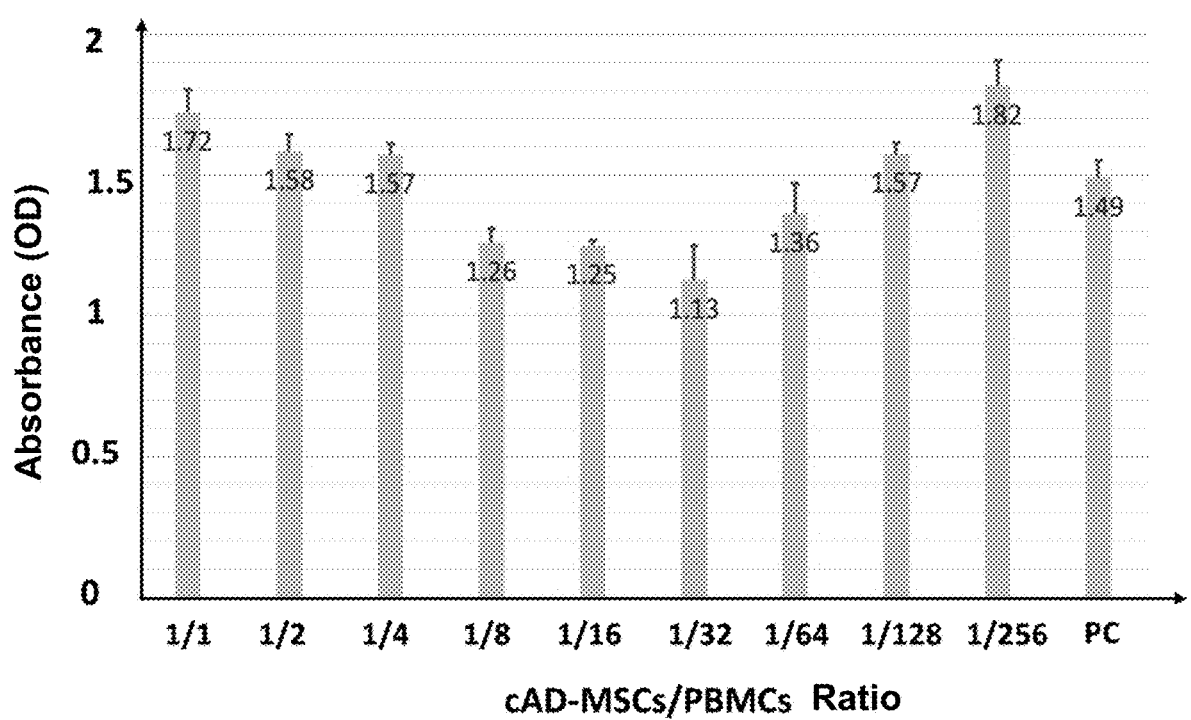
FIG. 6. Immunosuppressive properties of cAD-MSCs. $1.25 \times 10^4$ of cAD-MSCs/well (the ratio of cAD-MSCs/PBMCs: ⅛), $6.25 \times 10^3$ of cAD-MSCs/well (the ratio of cAD-MSCs/PBMCs: 1/16), $3.125 \times 10^3$ of cAD-MSCs/well (the ratio of cAD-MSCs/PBMCs: 1/32) and $1.56 \times 10^3$ of cAD-MSCs/well (the ratio of cAD-MSCs/PBMCs: 1/64) have significant inhibitory effects. In the mitogen proliferation assay, the inhibitory effect of cAD-MSCs on the proliferation of lymphocytes stimulated by mitosis is correlated with the number of cells in the well, and PC is treatment of ConA with PBMC as a positive control group.

5. Adipose-Derived Mesenchymal Stem Cell Immunomodulatory Effect:

The fifth subculture of cAD-MSCs was used for mitogen proliferation assays (MPA). In this test, it was confirmed that cAD-MSC would not stimulate lymphocyte proliferation and ConA was able to promote mitosis, in addition, PBMC stimulated with mitotic ConA was used as a positive control group (FIG. 5, PC). FIG. 6 showed the effect of PBMC on the proliferation stimulated by ConA in the presence or absence of cAD-MSCs. The results showed that when the ratio of cAD-MSCs/PBMC was ⅛, ¹⁄₁₆, and ¹⁄₃₂, ConA-facilitated cell proliferation could be meaningfully inhibited. It was showed that cAD-MSCs were able to inhibit lymphocyte proliferation, demonstrating its important role in immunosuppression.

Figure 7:
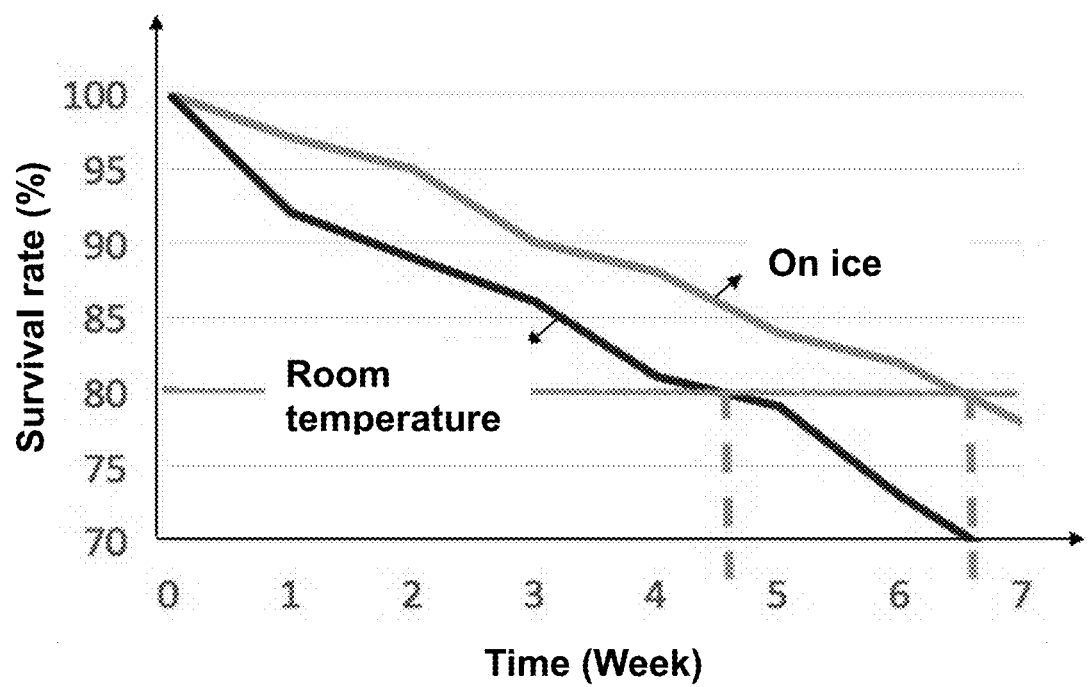
FIG. 7. Cell survival rate of cAD-MSC in eye drops. Eye drops containing cAD-MSC are stored in the dark at 4° C. for 6 hours or longer, and in the dark for 4 hours or longer at room temperature, the survival rate is able to be maintained at 80%.

6. Adipose-Derived Mesenchymal Stem Cell Survival Rate in Eye Drops:

As shown in FIG. 7, cAD-MSCs in the eye drops was able to be stored in the dark at 4° C. for 6 hours or longer, and in the dark at room temperature for 4 hours or longer to maintain 80% of survival rate. The cAD-MSCs eye drops used in our clinical trials were stored in the dark at 4° C. and applied topically within 2 hours, and according to the experimental results, the survival rate of cAD-MSCs at this time was 90%.

Example 2. Clinical Trials-Efficacy of Topical cAD-MSCs

Material and Method

1. Patients Inclusion and Exclusion Criteria:

The clinical trials were approved by the National Taiwan University Veterinary Hospital (Clinical Research No.: 000030). All patients in this study were NTUVH patients admitted between March 2018 and September 2018. They all underwent a comprehensive ophthalmic examination to confirm the diagnosis of KCS by the same veterinarian (LNW). Prior to the experimental treatment, all dog owners signed a written consent, declaring that they fully consented and fully understood the pathogenesis, clinical signs and traditional treatment methods of KCS and the safety and process of topical cAD-MSCs treatment. After the diagnosis of KCS was confirmed, the dogs were included in the study regardless of gender, breed or age. The diagnosis of canine KCS was based on medical history, clinical signs and criteria, and the diagnostic method was to measure the basal and reflective production of tear fluid by using SST. All KCS patients underwent a comprehensive physical and ophthalmic examination before being included in the study to determine whether they had any major eye diseases that might affect the outcome, and congenital, metabolic, infectious, drug-induced, neurological, radioactive and iatrogenic KCS were further excluded. In addition, patients who had been treated topically or systemically with any of the following drugs within 14 days prior to the study, including the following drugs; corticosteroids, atropine, pilocarpine, sulfa-containing drugs, or immunosuppressants such as cyclosporine A (CsA), pimecrolimus or tacrolimus, were also excluded, because these drugs might affect the immune system or induce KCS.

Figure 8:
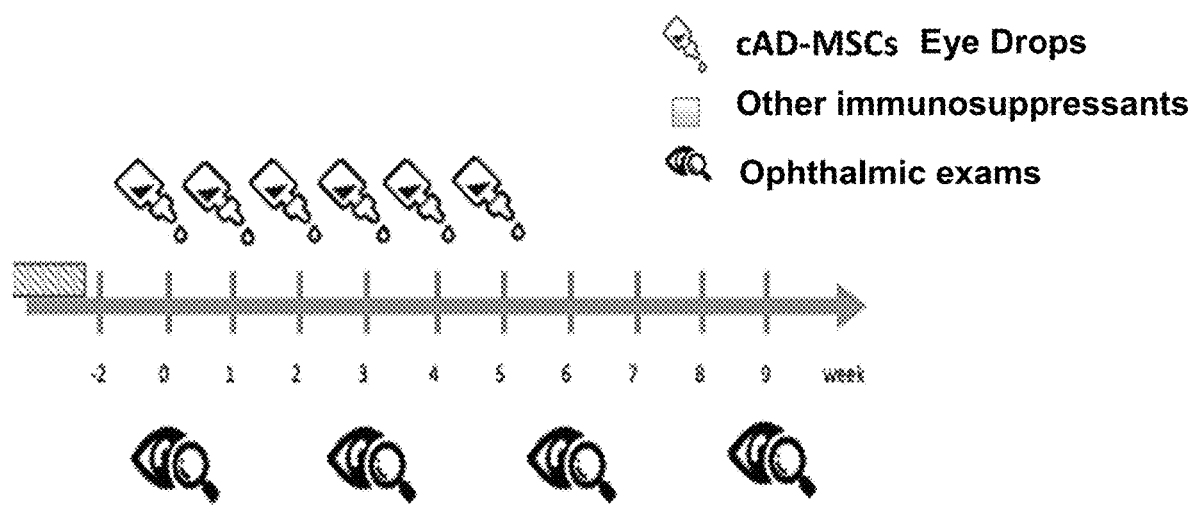
FIG. 8. Timeline for treatment and clinical evaluation. All patients are administered with cAD-MSCs eye drops containing $2 \times 10^6$ cells/50 μL PBS once a week for 6 consecutive weeks. In addition, all patients undergo 4 complete ophthalmic examinations before treatment, and at week 3, 6 and 9 after treatment. It is also confirmed that all patients of Group 2 have stopped using immunosuppressants for at least 14 days.

2. Grouping and Medical Treatment Protocols:

All included KCS patients were divided into two groups based on past medical history. Group 1: no history of treatment with immunosuppressants; Group 2: no response to previous immunosuppressive therapy. In particular, discontinuation of the use of any immunosuppressive agents for at least 14 days was confirmed for all patients in Group 2. Treatment was performed by topical administration of cAD-MSCs eye drops to confirm that the treatment was able to promote the production of tear fluid and to improve clinical signs of KCS. All patients were treated with topical administration of cAD-MSCs eye drops. The course lasted for 6 weeks, and 50 μL of eye drops containing 2×10$^6$ cAD-MSC cells were administered once a week, and all patients underwent 4 complete ophthalmic examinations before treatment (baseline), during treatment (week 3 and week 6) and after treatment (week 9). The schedule for treatment and clinical evaluation are shown in FIG. 8. During the efficacy study, the results of the ophthalmic examination were not informed, and the owners of all patients made evaluation of the treatment at week 9 using a numeric rating scale (NRS).

3. Clinical Evaluation:

At the time of trial recruitment, all patients had full physical and ophthalmic examinations before, during, and after treatment (baseline, week 3, 6, and 9). In addition, a complete medical history was recorded during the course of treatment, especially the dog owners' observation of clinical improvement and/or deterioration of the condition. The complete ophthalmic examination included: (1) Schirmer tear test (STT): STT was mainly used to evaluate the production of aqueous tear fluid. STT-1 (Schirmers tear test-1) was commonly used to measure the production of basal and reflective tear fluid. When the STT-1 value was not more than 15 mm/min, it was considered abnormal. The examination method was to fold a strip at the notch and placed the folded end inside the lower eyelid about 2 to 3 mm nasal to the lateral canthus for 1 minute; (2) Tear break-up time (TBUT) measurement: TBUT was mainly used to evaluate evaporative dry eye diseases, the examination method was to drop fluorescein into the tear film of the patient and manually open the eyelid so that the eye would not blink, at the same time the tear film was observed under the wide cobalt blue illumination of a slit lamp biomicroscope. The TBUT was recorded as the time (seconds) required for the first dry spot to appear in the tear film. TBUT less than 15 seconds was considered abnormal; (3) Fluorescein dye tested by using fluorescent paper: This test was used to examine the presence or absence of corneal ulcers, if the test result was positive, the patient would be excluded from the study; (4) Tear fluid osmolarity measurement: An i-Pen® Vet Osmolarity test sensor was inserted into an i-Pen® system (I-MED Pharma Inc., Dollard-des-Ormeaux, Quebec, Canada), then the tip end of the sensor on the conjunctiva of the lower eyelid was pressed without immersing the tip end of the sensor in the liquid surface of lower tear meniscus; The i-Pen® Vet osmolarity test sensor was used, the tear fluid osmolarity of normal dogs ranged from 296 to 339 mOsms/L; (5) Clinical signs of KCS evaluated by using slit-lamp biomicroscopy. In addition, the Digital Rating Scale (NRS) was used by both the owners and the veterinarian to score the severity of mucus secretions, conjunctival hyperemia, and corneal changes in dogs. Table 1 lists the scores from 1 to 5 corresponding to the clinical symptoms. In addition, one year after the end of treatment with topical cAD-MSCs, the owners were contacted by telephone, clinical signs of the patients were asked and the severity of mucus secretions, conjunctival hyperemia, and corneal changes evaluated by the same digital rating scale was obtained.

TABLE 1

Table of digital rating scale of clinical signs

| | | |
|---|---|---|
| Mucoid discharge | 5 = severe | Mucopurulent crust, stinky |
| | 4 = advanced | Yellowish, mucoid discharge, smelly |
| | 3 = moderate | Yellowish, sticky discharge |
| | 2 = lightly | Clear, but discharge volume increased |
| | 1 = normal | Absent discharge |
| Conjunctival hyperemia | 5 = severe | Diffuse beefy red |
| | 4 = advanced | Individual vessels not easily discernible |
| | 3 = moderate | More diffuse, deeper crimson red |
| | 2 = lightly | Vessels definitely injected above normal |
| | 1 = normal | Vessels normal |

TABLE 1-continued

Table of digital rating scale of clinical signs

| | | |
|---|---|---|
| Corneal change | 5 = severe | Opaque, iris invisible with pigmentation, keratitis |
| | 4 = advanced | Opalescent areas, no details of iris visible |
| | 3 = moderate | Easily discernible translucent area, details of iris slightly obscured |
| | 2 = lightly | Scattered or diffuse areas, details of iris clearly visible |
| | 1 = normal | No opacity |

4. Statistical Analysis:

Statistical analysis was done by using the GraphPad Prism 7 software to evaluate the efficacy of CAD-MSCs topically administered to the patients. Intra-group comparisons of STT-1, TBUT, and tear fluid osmolarity at the baseline, and at week 3, 6, and 9 were analyzed by the analysis of variance (ANOVA), followed by inter-group comparison with the baseline group by using the Bonferroni correction. NRS was an evaluation and analysis of clinical signs by using a two-sample Wilcoxon signed-rank test. When the probability value P of the analysis result was less than 0.05, it was considered to be statistically significant, wherein * indicates $P<0.05$,  indicates $P<0.01$, * indicates $P<0.001$, and **** indicates $P<0.0001$. All data are shown as mean±SEM (standard error of the mean).

Results

1. Subjects in Clinical Trials:

In this study, from April 2017 to June 2017, a total of 61 patients were recruited, among then the age distribution ranged from 6 months to 18 years, and the average age was 8.1 years. All patients underwent a comprehensive ophthalmic examination to confirm KCS. Among them, 28 patients met the KCS clinical criteria, but 5 patients with congenital, neurogenic, and infectious KCS were excluded. Finally, a total of 23 patients were included in this clinical trial. These patients were divided into two groups according to the presence or absence of medical history of immunosuppressive therapy. Group 1: 23 eyes of 12 dogs without medical history of immunosuppressive therapy, 1 of the patients suffered from unilateral KCS. Group 2: 21 eyes of 11 dogs that did not respond to previous immunosuppressive therapy, and one eye was excluded because the eye was removed due to refractory glaucoma secondary to lens dislocation. Therefore, the total number of eyes evaluated in this study was 44. The average age of the first group was 7.91±3.33 years (ranging from 5 to 15 years), and the average age of the second group was 8.83±3.79 years (ranging from 1 to 14 years). Eleven dogs were female dogs, two were sexually intact females, nine were neutered males, and one was sexually intact male. Most subjects were purebred, representing 9 breed types, with only one mongrel. Eleven patients in Group 2 did not respond to continuous immunosuppressive therapy for an average of 2 years and 4 months (ranging from 4 months to 5 years), wherein Optimmune® (n=1), 1% to 2% cyclosporin A complex corn oil (n=6) or 0.03% tacrolimus (n=5) were used as previous immunosuppressants. Table 2 shows the information of each patient more clearly.

TABLE 2

Information and ophthalmic examination results of each patient

| Age | Gender | Breed type | STT (OD/OS) | ipen (OD/OS) | TBUT (OD/OS) |
|---|---|---|---|---|---|
| 13 | NM | Beagle | 0/0 | 290/288 | 0/0 |
| 15 | NM | Schnauzer | 0/0 | 280/285 | 0/0 |
| 6 | NF | Dachshund | 3/9 | 294/278 | 6/10 |

TABLE 2-continued

Information and ophthalmic examination results of each patient

| 6  | NF | Dachshund | 12/—  | 279/—   | 3/— |
|----|----|-----------|-------|---------|-----|
| 7  | IF | Poodle    | 6/6   | 279/289 | 3/3 |
| 7  | NF | Poodle    | 14/7  | 279/289 | 1/3 |
| 10 | NM | Maltese   | 3/11  | 279/275 | 3/5 |
| 7  | NF | Maltese   | 0/3   | 338/317 | 2/2 |
| 5  | NF | Maltese   | 6/0   | 338/317 | 2/2 |
| 5  | NM | Yorkshire | 12/9  | 338/317 | 3/2 |
| 6  | IM | Yorkshire | 9/8   | 337/340 | 5/6 |

NM: male(neutered), NF: female(neutered), IM: male(intact), IF: female (intact),
OD: right eye, OS: left eye

| Age | Gender | Breed type | STT (OD/OS) | ipen (OD/OS) | TBUT (OD/OS) | Imunosuppressants/ Duration of therapy Medical history | |
|-----|--------|------------|-------------|--------------|--------------|-----------|-----------|
| 1  | IF | Yorkshire | 10/—  | 287/—   | 3/—  | 2% CsA     | 1 Y       |
| 6  | NM | Mixed     | 17/21 | 294/286 | 11/9 | 2% CsA     | 5 Y       |
| 14 | NM | Dachshund | 8/3   | 291/283 | 3/3  | 1% CsA     | 3 Y       |
| 5  | NF | Pug       | 0/11  | 284/288 | 0/3  | 1% CsA     | 4 M       |
| 14 | NM | Yorkshire | 0/0   | 279/295 | 0/3  | 2% CsA/TA  | 2 Y + 1 Y |
| 8  | NF | Maltese   | 0/3   | 275/316 | 3/5  | TA         | 1 Y       |
| 9  | NF | Maltese   | 0/4   | 321/335 | 2/2  | TA         | 3 Y       |
| 10 | NF | Maltese   | 15/5  | 277/278 | 3/3  | 1% CsA     | 2 Y       |
| 8  | NM | Charles   | 0/0   | 293/279 | 3/0  | Optimmune  | 1 Y       |
| 13 | NM | Chihuahua | 0/18  | 337/304 | 0/3  | 1% CsA/TA  | 2 Y + 2 M |
| 9  | NF | Dachshund | 0/0   | 326     | 3/2  | 1% CsA     | 3 Y       |
| 9  | NF | Poodle    | 10/5  | 293     | 1/2  | TA         | 4 Y       |

Figure 9:
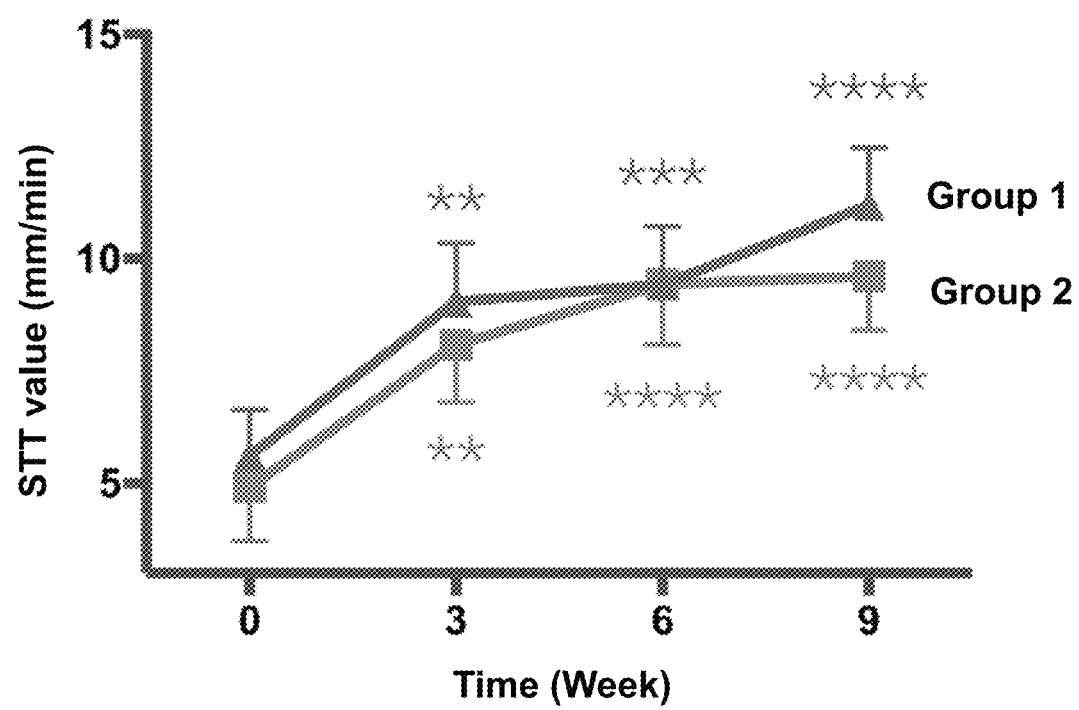
FIG. 9. Effect of treatment on STT-1. The effect of Group 1 (no history of immunosuppressants) and Group 2 (no response to immunosuppressants) on tear fluid production. Each point represents the mean±SEM of 21 and 23 eyes, respectively.

NM: male(neutered), NF: female(neutered), IM: male(intact), IF: female (intact),
OD: right eye, OS: left eye, CsA: Cyclosporine A, TA: Tacrolimus, Y: year, M: month 2. Efficacy of Topically Administered cAD-MSC-Containing Eye Drops 50 μL of eye drops containing 2×10$^6$ cAD-MSCs was topically administered to all patients for 6 consecutive weeks, once every week, and a comprehensive ophthalmic examination was conducted at the baseline, and week 3, 6 and 9 (FIG. 8). The results showed that the STT-1 mean values for Group 1 and Group 2 at baseline were 5.1±4.7 mm/min (n=21) and 5.2±6.6 mm/min (n=23), respectively. The STT-1 mean values of Group 1 at week 3, 6 and 9 increased by 3.17, 4.53, and 4.70 mm/min, respectively; and the STT-1 mean value of Group 2 at week 3, 6, and 9 increased by 3.43, 3.80 and 5.53 mm/min, respectively. A statistically significant improvement was observed in both groups as compared to the baseline (P<0.0001), but the difference between two groups was not statistically significant (P=0.6120) (FIG. 9). In general, patients who responded well to the treatment were defined as having an increase in the STT-1 value of more than 5 mm/min. Therefore, at week 3, 28.6% of the patients in Group 1 and 30.4% of the patients in Group 2 had a good response to cAD-MSC treatment, and at week 6, nearly half of the patients in both groups (47.6% and 47.8%, respectively) had a good response to the treatment. In the last ophthalmic examination at week 9, the percentage of patients in Group 1 and Group 2 who had good responses reached 57.1% and 56.5%, respectively. No statistical difference was found between the two groups.

Figure 10:
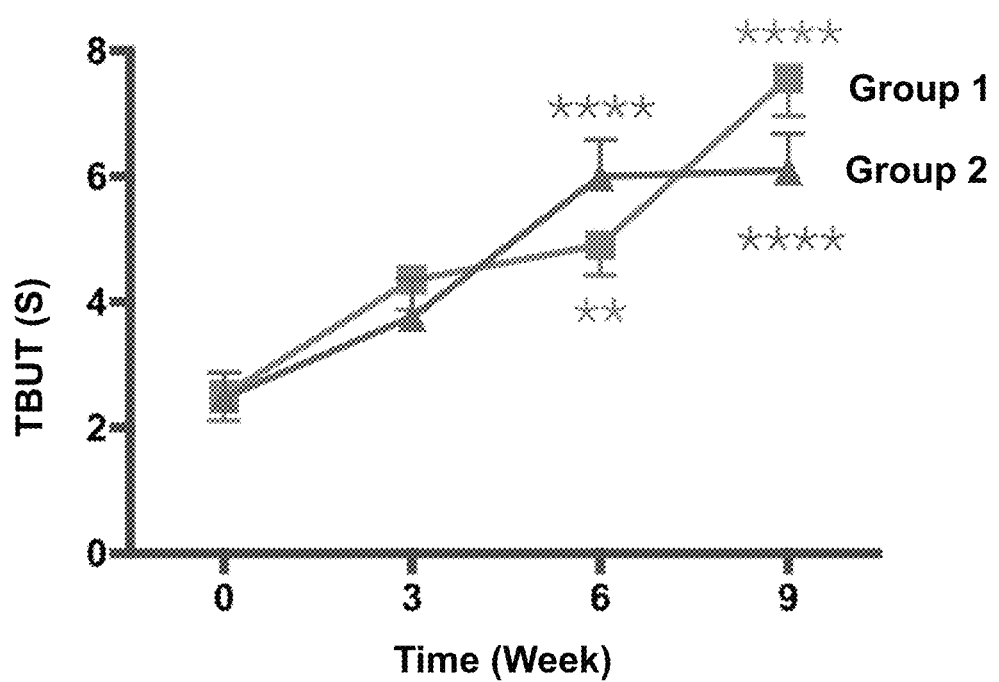
FIG. 10. Effect of treatment on TBUT. The effect of Group 1 (no history of immunosuppressants) and Group 2 (no response to immunosuppressants) on the quality of tear film. Each point represents the mean±SEM of 21 and 23 eyes, respectively.

The TBUT test results showed that the TBUT mean value of the patients in Group 1 was 2.65±2.48 seconds, and the TBUT mean value of the patients in Group 2 at baseline was 2.92±2.48 seconds. As shown in FIG. 10, at week 3, 6 and 9, the TBUT mean value of Group 1 increased by 1.28, 3.52, and 3.62 seconds, respectively, and at week 3, 6 and 9, the TBUT mean value of Group 2 increased by 1.83, 1.39, and 5.04 seconds, respectively. An increase in TBUT was observed in both treatment groups and there was a statistically significant improvement as compared to the baseline (P<0.0001), but the difference between two groups was not statistically significant (P=0.4951).

Figure 11:
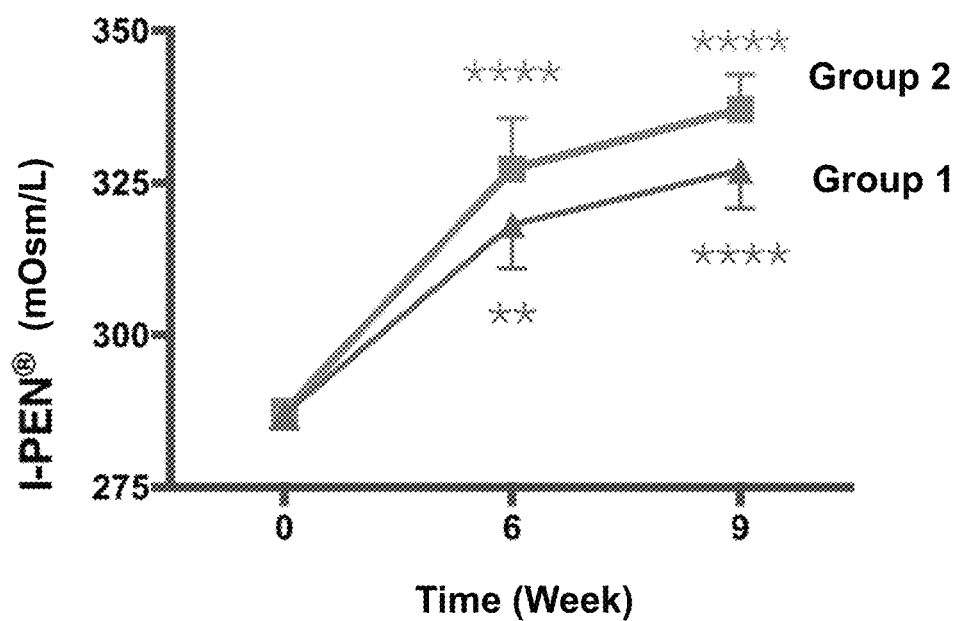
FIG. 11. Effect of treatment on tear fluid osmolarity. The effect of Group 1 (no history of immunosuppressive agents) and Group 2 (no response to immunosuppressive agents) on the tear fluid osmolarity. Each point represents the mean±SEM of 21 and 23 eyes, respectively.

The tear fluid osmolarity measurements by using i-PEN® were conducted only at baseline, week 6 and 9 due to high examination cost. As shown in FIG. 11, the average osmolarity of Group 1 measured at baseline, week 6 and week 9 was 287.09, 318.18 and 327.09 mOsms/L, respectively, and Group 2 was 287.46, 327.36 and 337.09 mOsms/L, respectively, both groups showed a statistically significant improvement as compared to the baseline (P<0.0001), but the difference between two groups was not statistically significant (P=0.1732). The normal range of tear fluid osmolarity using i-Pen® Vet was from 296 to 339 mOsms/L, and most patients after treatment exhibited tear fluid osmolarity comparable to the standard.

Figure 12:
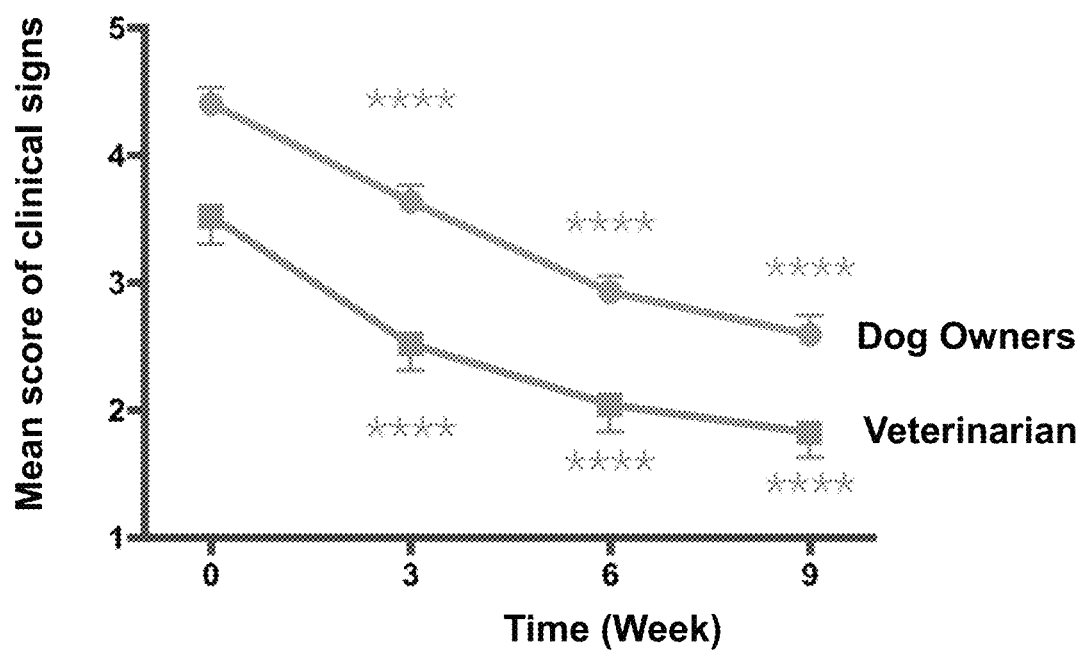
FIG. 12. Effect of treatment on clinical symptoms. NRS is used by dog owners and veterinarians to evaluate clinical signs. Each point represents the mean fractional value±SEM of the mucus secretions, conjunctival hyperemia, and corneal changes of 23 dogs, showing a statistically significant difference as compared to the baseline.
Figure 13:
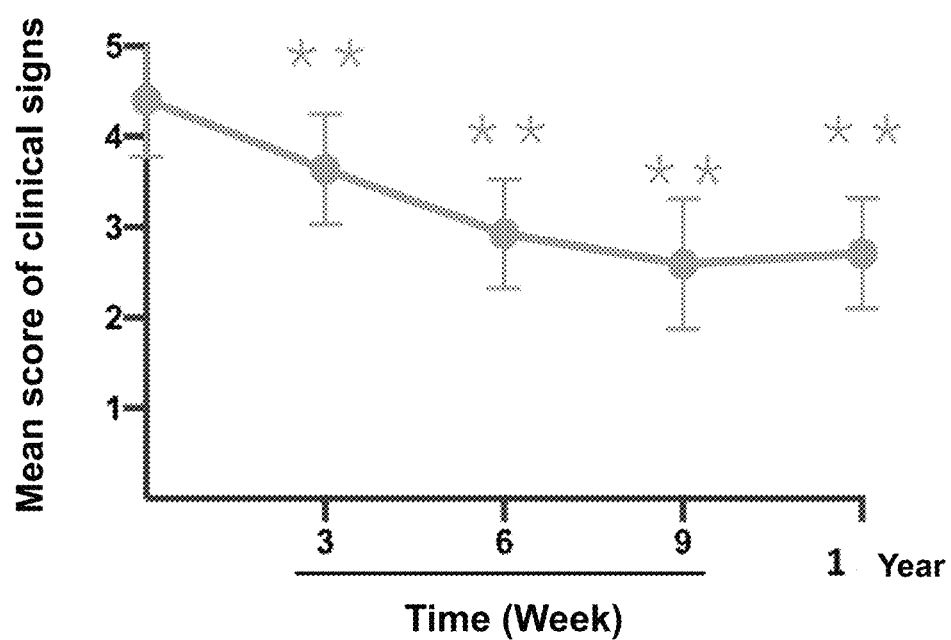
FIG. 13. Effect of treatment on clinical symptoms evaluated by dog owners. NRS is used by dog owners to evaluate clinical signs. Each point represents the mean±SD of the mucus secretions, conjunctival hyperemia, and corneal changes of 23 dogs. As compared to the baseline, there is a statistically significant difference.

The clinical signs of the patients in both groups were evaluated and observed by the veterinarian and the owners. The scores of the Digital Rating Scale (NRS) were between 1 and 5 and were used to evaluate the severity of the clinical signs of KCS. At the baseline, the mean total scores (maximum total score of 15) of the mucoid discharge, conjunctival hyperemia, and corneal changes in all patients were 4.40 and 3.52, respectively. The mean total scores evaluated by the owners at week 3, 6 and 9 were 3.64, 2.93 and 2.59, respectively. At the same time, the mean total scores evaluated by the veterinarian at week 3, 6 and 9 decreased to 2.53, 2.04 and 1.83, respectively. As shown in FIG. 12, the clinical outcomes were significantly improved after the treatment as compared to the baseline (P<0.0001). The dog owners conducted a one-year clinical follow-up of all patients. As shown in FIG. 13, the mean total score of all patients after one year with respect to mucus secretions, conjunctival hyperemia, and corneal changes was 2.71 (P<0.0001).

Example 3. Patients Having No Medical History of Immunosuppressive Therapy

Case No. 1071359, Running, a 10-year-old neutered male Maltese dog who had a history of ocular inflammation for one year. In the past year, the owner noticed excessive blinking and discharge of mucus. Examination revealed that mucus was discharged in the area surrounding periorbital hairs. In a slit lamp examination, corneal neovascularization and keratitis were found in both eyes, while the right eye was affected more seriously. The STT results showed that the STT-1 value of the right eye was 3 mm/min, revealing a severe KCS. After being treated with cAD-MSCs, the STT-1 value increased to 10 mm/min. The dog owner also observed that the patient looked more relieved than before, and more detailed ophthalmic examination results and photo records are presented in Table 3 and FIG. 14A.

TABLE 3

| | Case 1 | | | |
|---|---|---|---|---|
| | Before treatment Baseline | After treatment Week 3 | After treatment Week 6 | After treatment Week 9 |
| STT-1 | 3/11 | 5/17 | 13/18 | 10/18 |
| TBUT | 3/5 | 3/3 | 10/10 | 8/10 |
| i-PEN | 279/295 | 278/280 | 290/275 | 279/275 |
| Item | Discharge/hyperaemia/cornea | | | |
| Qwners Score | 5/5/5 | 4/4/4 | 3/3/3 | 3/3/3 |
| Veterinarian Score | 5/4/3 | 4/3/3 | 2/2/2 | 1/2/1 |

Example 4. Patients Having No Response to Currently Available Immunosuppressive Therapy Lele, a 14-year-old neutered male Yorkshire dog who had chronic KCS and a STT-1 value of 0 mm/min for 4 years. The patient had received a treatment of 2% cyclosporin A for more than 2 years and 0.03% tacrolimus for 1 year, but showed no response. Before being treated with cAD-MSCs, there were severe eye secretions, hyperemia and corneal changes. The dog owner indicated that the mucous rough skin had to be cleaned every day, otherwise the patient was unable to open its eyes. An ophthalmic examination revealed mucous rough skin around the periorbital hairs, severe corneal neovascularization, hyperpigmentation, and severe keratitis, the corneal transparency of both eyes was reduced, and the right eye was affected more seriously. After being treated with cAD-MSCs, the clinical outcomes were significantly improved. The dog owner indicated that the treatment had cured the severe eye diseases lasted for many years.

Figure 14:
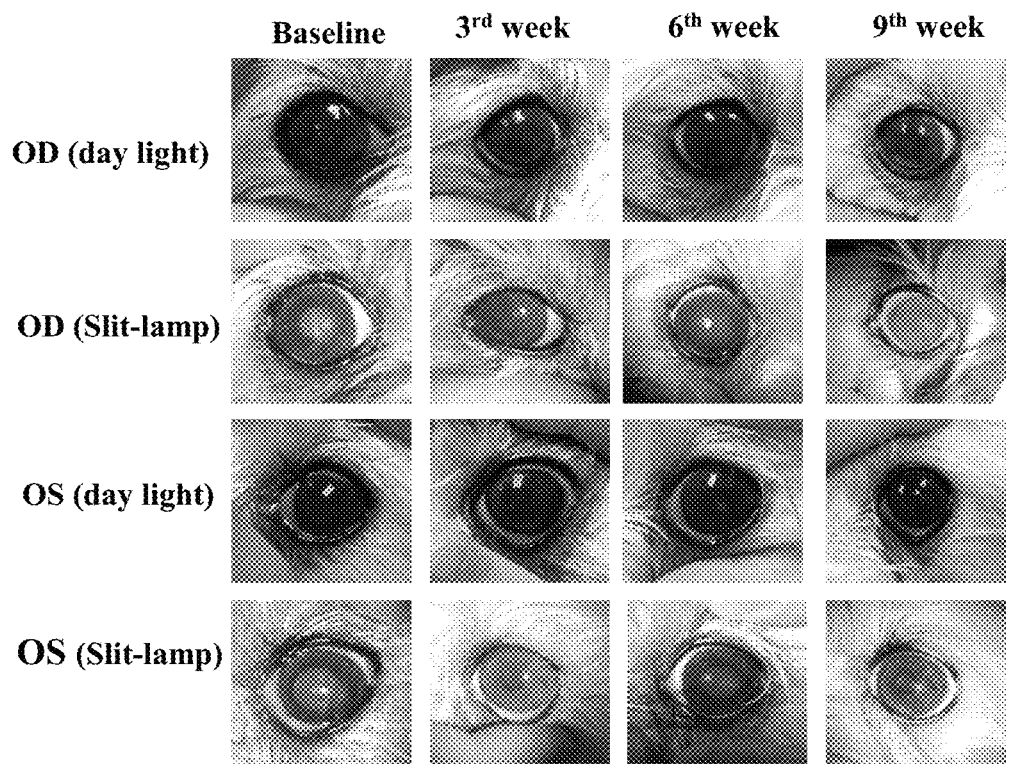
FIG. 14. Photographs of ophthalmic examinations before and after treatment of the patient with no history of immunosuppressive therapy (A) and photographs of ophthalmic examinations before and after treatment of the patient who did not respond to existing immunosuppressive therapy (B).
Figure 14:
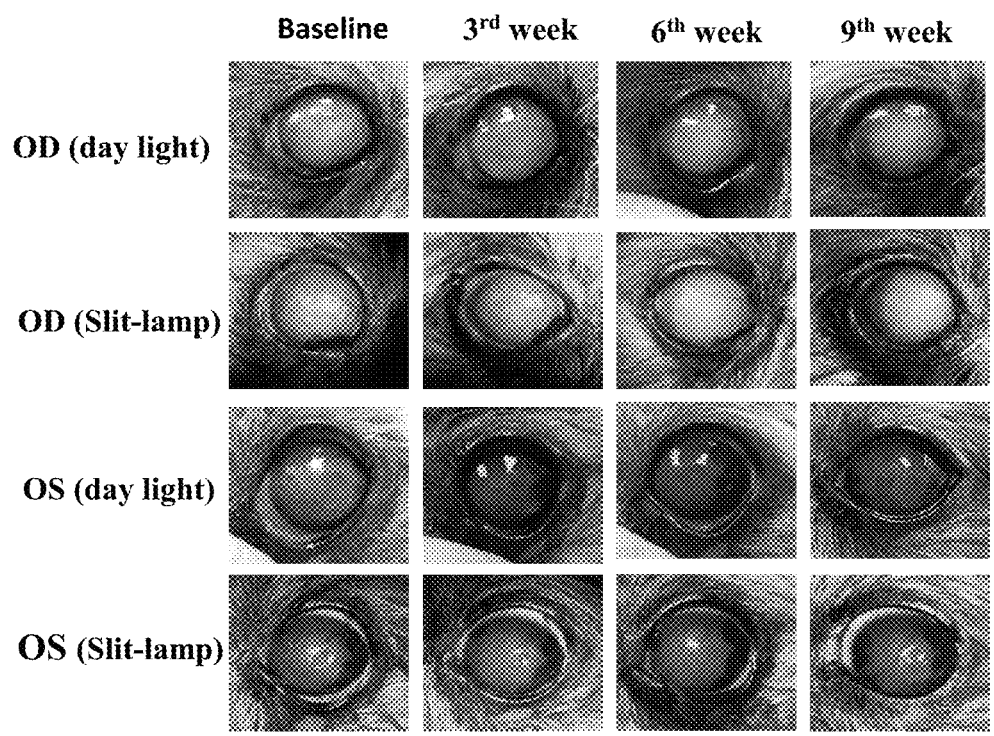

More detailed ophthalmic examination results and photo records are presented in Table 4 and FIG. 14B.

TABLE 4

| | Case 2 | | | |
|---|---|---|---|---|
| | Before Treatment Baseline | After treatment 3rd week | After treatment 6th week | After treatment 9th week |
| STT-1 | 0/0 | 3/3 | 3/5 | 5/5 |
| TBUT | 1/3 | 3/5 | 6/10 | 8/9 |
| i-PEN | 279/295 | 300/326 | 341/332 | 351/349 |
| Item | Discharge/hyperaemia/cornea | | | |
| Qwners Score | 5/4/5 | 4/3/4 | 2/2/3 | 2/2/2 |
| Veterinarian Score | 5/5/5 | 4/4/4 | 3/2/2 | 2/1/2 |

What is claimed is:

1. A method of treating a subject suffering from dry eye syndrome, comprising: administering to said subject a pharmaceutical composition for treating dry eye syndrome, comprising an effective amount of adipose-derived mesenchymal stem cells, wherein the pharmaceutical composition is administered to the eye topically in the form of eye drops, wherein the eye drops are administered once a week for three to six consecutive weeks, and the dry eye syndrome is immune-mediated dry eye syndrome.

2. The method of claim 1, wherein the immune-mediated dry eye syndrome is Sjogren's syndrome.

3. The method of claim 1, wherein the subject is a mammal.

4. The method of claim 1, wherein the source of the adipose-derived mesenchymal stem cells is from a subject allogeneic to the subject.

5. The method of claim 1, wherein the solution of the eye drops is phosphate buffered saline.

6. The method of claim 1, wherein the concentration of the effective amount of adipose-derived mesenchymal stem cells is from $1 \times 10^6$ to $5 \times 10^6/50$ μL.

7. The method of claim 1, wherein the subject suffering from dry eye syndrome is a subject who does not respond to an immunosuppressive therapy.

8. The method of claim 7, wherein the immunosuppressive therapy comprises a treatment of administering cyclosporine A, pimecrolimus, tacrolimus or any combination thereof.

* * * * *